(12) United States Patent
Munro et al.

(10) Patent No.: US 6,447,798 B1
(45) Date of Patent: Sep. 10, 2002

(54) BIOADHESIVE COMPOSITIONS AND WOUND DRESSINGS CONTAINING THEM

(75) Inventors: Hugh Semple Munro, Chipping Camden; Mohammed Yasin, Saltley, both of (GB)

(73) Assignee: First Water Limited, Marlborough (GB)

( * ) Notice: Subject to any disclaimer, the term of this patent is extended or adjusted under 35 U.S.C. 154(b) by 0 days.

(21) Appl. No.: 09/770,561

(22) Filed: Jan. 26, 2001

(30) Foreign Application Priority Data

Apr. 23, 1996 (GB) ................................ 9909348
Jul. 31, 1998 (GB) ................................ 9816826
Mar. 24, 1999 (GB) ................................ 9906700
Jul. 30, 1999 (WO) .......................... PCT/GB99/02524

(51) Int. Cl.$^7$ .......................... A61L 15/16; A61K 9/70
(52) U.S. Cl. ................. 424/445; 424/443; 424/447
(58) Field of Search .................. 424/443, 445, 424/447

(56) References Cited

U.S. PATENT DOCUMENTS 5,352,508 A   10/1994   Cheong 5,670,557 A * 9/1997 Dietz et al. ................. 522/184

FOREIGN PATENT DOCUMENTS

| EP | 0676457 | 10/1995 |
| WO | WO 97/05185 | 2/1997 |
| WO | WO 97/24149 | 7/1997 |

* cited by examiner

Primary Examiner—Carlos Azpuru
(74) Attorney, Agent, or Firm—Kathleen Madden Williams; Palmer & Dodge LLP

(57) ABSTRACT

Water unstable bioadhesive compositions comprising an aqueous plasticiser, a cross-linking agent, a copolymer of a hydrophilic unsaturated water soluble firt monomer a hydrophobic unsaturated water-soluble second monomer, characterised in that they have: (i) a water activity of from 0.4 to 0.9; (ii) an elastic modulus at 1 rad/s of from 700 to 15,000 Pa; (iii) an elastic modulus at 100 rad/s of from 20000 to 40,000 Pa; (iv) a viscous modulus at 1 rad/s of from 400 to 14,000 PA; (v) a viscous modulus at 100 rad/s of from 1000 to 35,000 Pa; wherein the viscous modulus is less than the elastic modulus in frequency range of from 1 to 100 rad/s; amd wound dressings made from them.

11 Claims, 5 Drawing Sheets

G' 1 rad Vs Crosslinker Content (50% WATER)

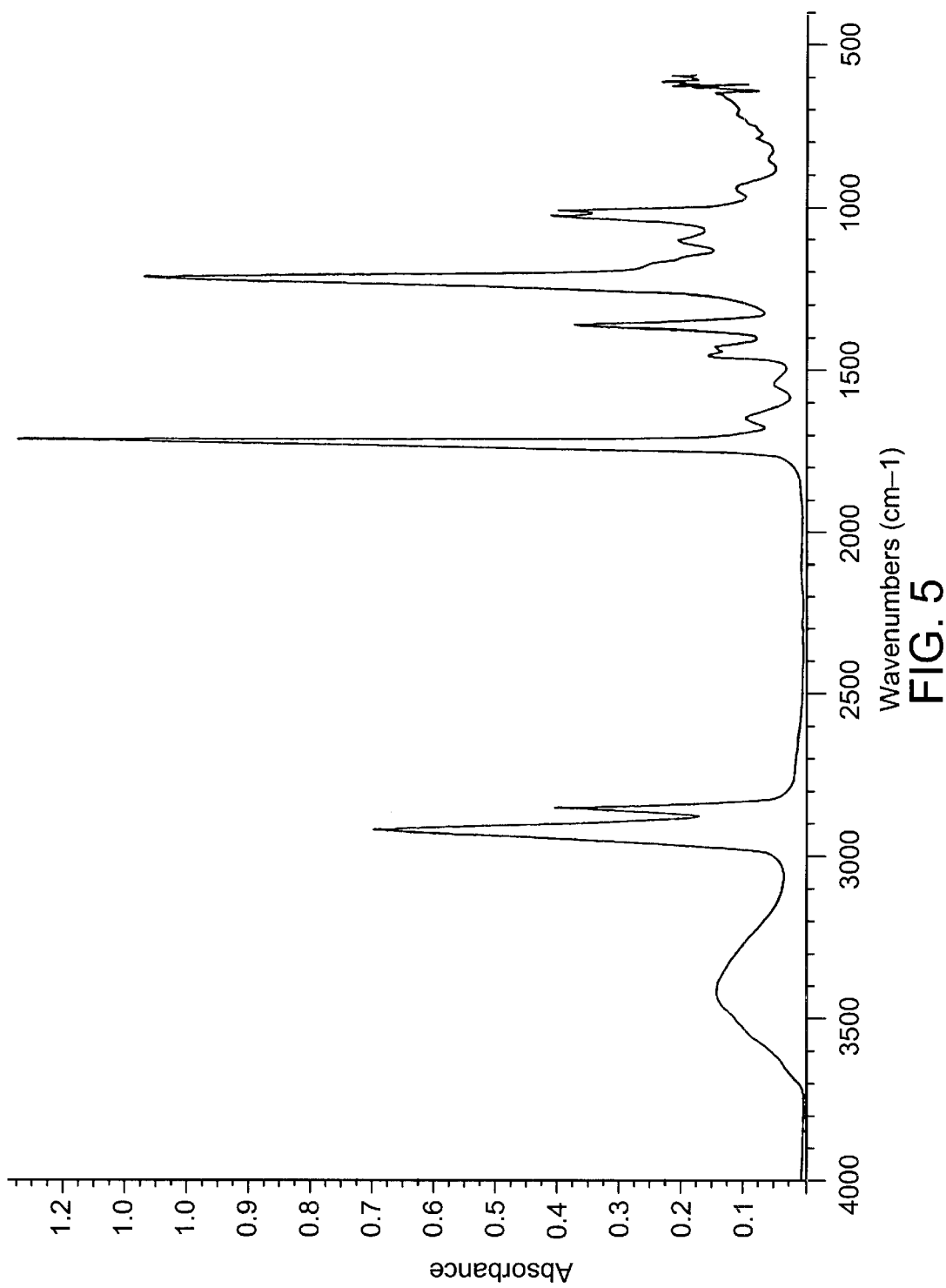

BIOADHESIVE COMPOSITIONS AND WOUND DRESSINGS CONTAINING THEM

RELATED APPLICATIONS

This application claims priority under 35 U.S.C. § 119(e) to GB 98/16826.3 filed Jul. 31, 1998, GB 99/06700.1 filed Mar. 24, 1999, GB 99/09348.6 filed Apr. 23, 1999 and also claims priority under 35 U.S.C. § 120 to PCT Application No. 99/02524 filed Jul. 30, 1999, the entireties of which are incorporated herein by reference.

FIELD OF THE INVENTION

This invention relates to bioadhesive compositions, particularly wound dressings comprising hydrogel compositions having bioadhesive properties.

BACKGROUND

One form of wound dressing commonly used comprises a perforated carrier material and a layer of hydrophilic coating which lies against the wound or sore. U.S. Pat. No. 5,352,508 (Cheong) discloses a net dressing in which the net is encapsulated by a hydrophilic tacky resin and wherein the resin encapsulated on the net leaves the majority of the apertures in the net substrate unoccluded. The hydrophilic tacky resin used as the coating is said to be a polymerised hydrogel.

An important feature for a wound dressing is that it should not adhere to the wound. This is in order that it is allowed to heal and to prevent damage to the wound on removal of the dressing. At the same time the wound dressing needs to adhere strongly to normal skin to prevent the wound dressing from coming off. Whilst it has been appreciated in the past that these features are important, there has been no understanding of how to achieve them in a hydrogel system.

It is an object of this invention to provide hydrogel skin adhesives possessing controlled and predictable adhesive properties which may be readily varied to suit different uses and, in the case of wound dressings or similar devices, different configurations or applications. It is also an object of the invention to provide such hydrogel skin adhesives which in addition may possess superior adhesion characteristics as compared to those commonly associated with bioadhesive hydrogels.

SUMMARY OF THE INVENTION

The performance of hydrogels as adhesives is related to the surface energetics of the adhesive and of the adherend (for example mammalian skin) and to the viscoelastic response of the bulk adhesive. The requirement that the adhesive wets the adherend to maximise the work of adhesion is well known. This requirement is generally met when the adhesive has a similar or lower surface energy to the adherend. The viscoelastic properties, in particular the elastic or storage modulus (G') and the viscosity modulus (G") are important. They are measured by dynamic mechanical testing at different rad/s. Their values at low rad/s (approximately 0.01 to 1rad/s) and high rad/s (100 to 1000 rad/s) has been related to the wetting/creep behaviour and peel/quick stick properties respectively. The choice, assembly and processing of the ingredients of the hydrogel adhesive are usually targetted at making a material with a balance of properties suitable for pressure sensitive adhesive applications. A balance between the quantities and nature of polymer, plasticiser and the degree of crosslinking/entanglement has to be achieved.

Whilst the presence of glycerol or other polyhydric alcohols in other reported formulations has been quoted to provide humectant properties to the hydrogel, it has been found that the most important parameter to preventing water loss is the activity of the water within the hydrogel which in turn depends on the nature and proportions of the other components and manner of processing.

Water activity in the hydrogel adhesive is primarily dependent on the water content and the nature of the polymeric components and the way in which they are processed. Water activity has been shown to have a better correlation with the growth of bacteria and moulds than water content. It has been found that organisms struggle to grow at water activities less than 0.8. Enzyme activity has also been reported to decrease significantly below activity of 0.8. Some wound dressings currently available not only have high water contents but also high water activity, greater than 0.99. Although these materials are sterilised, on opening the pack they may become subject to encouraging microbial growth. Water activity has also been found to influence the adhesivity of the hydrogel adhesive in that at water activities above about 0.75, they become less adhesive. A bioadhesive composition having a suitable balance of the characteristics discussed above has now surprisingly been found.

According to the invention there is provided a water unstable bioadhesive composition characterised in that it has:

(i) a water activity of from 0.4 to 0.9;
(ii) an elastic modulus at 1 rad/s of from 700 to 15,000 Pa;
(iii) an elastic modulus at 100 rad/s of from 2000 to 40,000 Pa;
(iv) a viscous modulus at 1 rad/s of from 400 to 14,000 Pa;
(v) a viscous modulus at 100 rad/s of from 1000 to 35,000 Pa;

wherein the viscous modulus is less than the elastic modulus in the frequency range of from 1 to 100 rad/s. Preferably the surface energetics of the composition is from 25 to 40 dynes.

Examination of the rheological properties of the compositions have been successfully used to characterise and differentiate adhesive behaviour. Typically the elastic modulus (G') and the viscous modulus (G") are measured over a range of 0.01–100 rad/s at a given temperature. For skin applications the appropriate temperature is 37° C. The moduli at low rad/s values relate to the initial bonding of the adhesive to skin and the higher to the changes in moduli values associated with de-bonding. Methods of measuring G' and G" are well known; for example a Rheometric Scientific RS-5 rheometer could be used.

The water activity of the composition can be measured using impedance methods with devices such as the Rotronic AWVC (manufactured by Rotronic). The activity of water may also be determined by placing the composition in environments of controlled humidity and temperature and measuring the changes in weight. The relative humidity (RH) at which the composition does not change weight corresponds to the activity of water in the gel (RH/100). The use of saturated salt solutions to provide the appropriate environmental conditions is well known. All compositions directly exposed to relative humidities less than that corresponding to the activity of water will be thermodynamically allowed to lose water. Exposure to greater relative humidities and the composition will gain weight.

The bioadhesive composition preferably comprises an aqueous plasticiser, a copolymer of a hydrophilic unsaturated water-soluble first monomer and a hydrophilic unsaturated water-soluble second monomer and a cross-linking agent, the first monomer having a tendency preferentially to enhance the bioadhesive properties of the composition.

Preferably the first monomer has a tendency also to enhance the mechanical strength of the composition according to the invention and/or the second monomer has a tendency preferentially to increase the water activity of the composition.

The bioadhesive composition is preferably obtainable by polymerising an aqueous reactive mixture comprising the said first monomer, the said second monomer and a crosslinking agent.

According to the invention, there is further provided a wound dressing which comprises a carrier material and the bioadhesive composition according to the invention. The carrier material is either encapsulated or coated by either of the bioadhesive compositions. Preferably it is coated, particularly on only one side.

According to the invention there is also provided a process for the preparation of a wound dressing according to the invention which process comprises either:

(a) coating or encapsulating a carrier material with an aqueous reaction mixture comprising the said first monomer, the said second monomer and a crosslinking agent, and curing the coating on the material; or (b) coating a carrier material with the bioadhesive composition according to the invention.

In preferred embodiments the first and second monomers will be acrylate based monomers selected for their ability to polymerise rapidly in water and having substantially the same molecular weight whereby in a mixture of the two the relative proportions may be varied without significantly altering the molar characteristics of the composition.

The first monomer is preferably a compound of formula

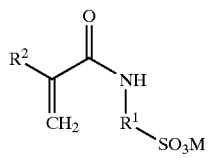

(I)

wherein $R^1$ is an optionally substituted hydrocarbon moiety, $R^2$ is hydrogen or optionally substituted methyl and ethyl, and M represents hydrogen or a cation.

$R^1$ is preferably an optionally substituted alkyl, cycloalkyl or aromatic moiety. Preferably $R^1$ represents a saturated moiety or an aromatic moiety. $R^1$ preferably contains from 3 to 12 carbon atoms, more preferably from 3 to 6 carbon atoms. A preferred moiety which $R^1$ represents is

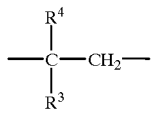

wherein $R^3$ represents hydrogen or an optionally substituted straight or branched chain alkyl group possessing from 1 to 6 carbon atoms and $R^4$ represents an optionally substituted straight or branched chain alkyl group possessing from 1 to 6 carbon atoms.

The second monomer is preferably a compound of formula

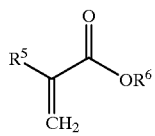

(II)

wherein $R^5$ represents hydrogen or optionally substituted methyl or ethyl, $R^6$ represents hydrogen, a cation or $R^7SO_3$ wherein $R^7$ represents an optionally substituted alkylene moiety of 1 to 4 carbon atoms. Preferably $R^7$ represents optionally substituted n-propyl.

$R^1$, $R^2$, $R^3$, $R^4$, $R^5$ and $R^7$ are optionally substituted by a group which preferably has a tendency to increase the water solubility of the compound. Suitable groups will be well known to a person of skill in the art. A preferred optional substituent is a hydroxyl, amino or ammonium group or a halogen (e.g. chlorine, bromine, or iodine) atom. A suitable cation is an alkali metal cation, especially sodium or potassium.

Most preferably the first monomer is 2-acrylamido-2-methylpropanesulphonic acid or an analogue thereof or one of its salts, e.g. an alkali metal salt such as a sodium, potassium or lithium salt. The second monomer preferably is acrylic acid or an analogue thereof or one of its salts, e.g. an alkali metal salt such as sodium, potassium or lithium or it preferably is a polymerisable sulphonate or a salt, e.g. an alkali metal salt such as a sodium, potassium or lithium salt, of acrylic acid (3-sulphopropyl)ester or an analogue thereof. Particular preferred examples of these respective monomers are the sodium salt of 2-acrylamido-2-methylpropanesulphonic acid, commonly known as NaAMPS, and acrylic acid (3-sulphopropyl)ester potassium salt, commonly known as SPA. NaAMPS is available commercially at present from Lubrizol as either a 50% aqueous solution (reference code LZ2405) or a 58% aqueous solution (reference code LZ2405A). SPA is available commercially in the form of a solid from Raschig.

The total monomer content in the aqueous reactive mixture is preferably from 15% to 60% by weight, preferably from 20% to 50% by weight.

One advantage of the bioadhesives and wound dressings according to the present invention is that they do not adhere to wet skin. This is measured by the decrease in peel strength of a hydrogel when it absorbs water, for example more than 3% by weight water. It has been found that this decrease in peel strength is optimal for certain weight ratios of monomers. A further advantage of the composition according to the invention is that tests have shown that such compositions are readily sterilisable. Consequently they have particular application in products having medical uses, such as wound dressings.

Where the first monomer is a salt of AMPS and the second monomer is a salt of acrylic acid, the ratio by weight of the first monomer to the second monomer is preferably not less than 2:1 and preferably not less than 3:1. Where the first monomer is a salt of AMPS and the second monomer is a salt of acrylic acid (3-sulphopropyl)ester, the ratio by weight of the first monomer to the second monomer is preferably not less than 1:10, preferably not less than 1:1.

The first monomer is preferably included in an amount by weight of from 1% to 60%, more preferably from 5% to 50%, most preferably from 15% to 40%. The second monomer is preferably included in an amount by weight of from 1% to 50%, preferably from 10% to 30%, most preferably from 10% to 20%. The crosslinker is preferably included in an amount of from 0.01% to 2%, more preferably from 0.1 to 2% by weight. The balance of the composition preferably comprises an aqueous plasticiser.

One advantage of the first and second monomers is that it has been found that high monomer content solutions can be achieved (approximately 75%). It has also been found that the second monomer is soluble in polyhydric alcohols such as glycerol, and addition of glycerol to the first and second monomer mixture enhances the solubilisation process. It has been found that the combination of the two monomers enables a greater control over water content than can be achieved otherwise. This can be important because it has also been found that compositions made with the final water content as an integral part of the pre-gel mix have different properties from those made with an excess of water and then dried to the final composition. For example, hydrogels with a final composition obtained be the evaporation of water generally have lower elastic or storage moduli than those made with no evaporation of water. To obtain similar levels of elastic moduli, the amount of crosslinker required in the former materials is higher. The evaporation of water and extra crosslinker add to the cost of the process. This problem is avoided by the present invention where a final drying step is generally not required.

Conventional crosslinking agents are used to provide the necessary mechanical stability and to control the adhesive properties of the composition. Typical crosslinkers include tripropylene glycol diacrylate, ethylene glycol dimethacrylate, alkoxylated triacrylate, polyethylene glycol diacrylate (PEG400 or PEG600), methylene bis acrylamide.

The aqueous reactive mixture optionally further comprises a surfactant, an additional monomer, an electrolyte, a processing aid (which is preferably a hydrophobic polymer), a water soluble polymer suitable for forming an interpenetrating polymer network, a non-hydrophilic polymer, an antimicrobial agent (e.g. citric acid, stannous chloride) and/or, for drug delivery applications, pharmaceutically active agents, the latter being designed to be delivered either passively (e.g. transdermally) or actively (e.g. iontophoretically) through the skin.

The process used to prepare bioadhesive compositions in accordance with the invention comprises mixing the ingredients to provide a reaction mixture in the form of an initial pre-gel aqueous based liquid formulation, which is then converted into a gel by a free radical polymerisation reaction. This may be achieved for example using conventional thermal initiators and/or photoinitiators or by ionizing radiation. Photoinitiation is a preferred method and will usually be applied by subjecting the pre-gel reaction mixture containing an appropriate photoinitiation agent to UV light after it has been spread or coated as a layer an siliconised release paper or other solid substrate. The processing will generally be carried out in a controlled manner involving a precise predetermined sequence of mixing and thermal treatment or history. One preferred feature of the process according to the invention is that no water is removed from the hydrogel after manufacture.

BRIEF DESCRIPTION OF THE DRAWINGS

FIG. 5 depictss the fourier transform infrared attentuated total reference (FTIR ATR) spectra for the gel of Example 10b that is formed after polymerization. The FTIR ATR spectra was obtained using a germanium crystal and an approximate sampling depth of 0.25 $\mu$m.

DETAILED DESCRIPTION

Additional Monomer

Figure 1:
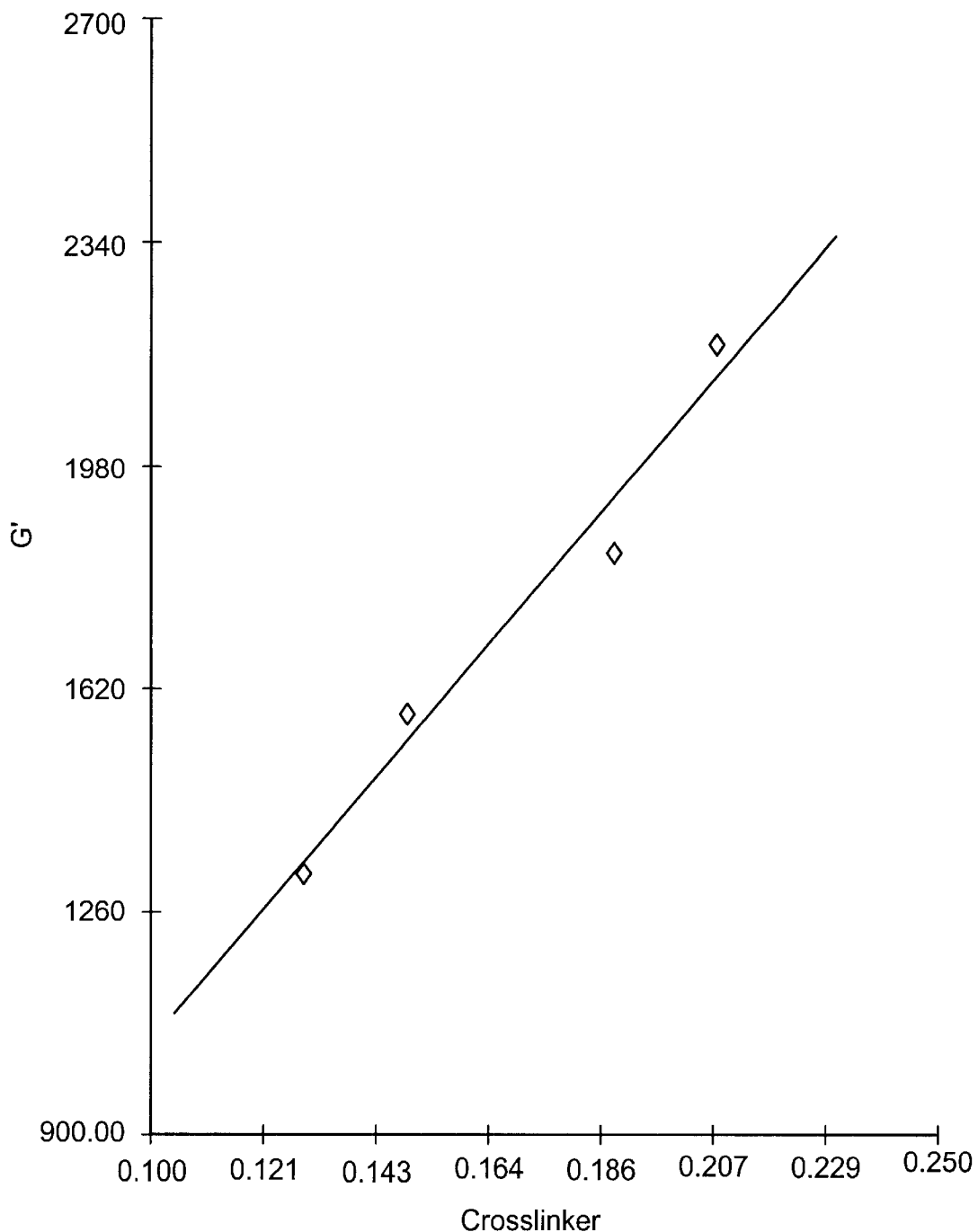
FIG. 1 is a graph depicting the linea correlation of elastic modulus G' values at 1 rad with increasing amounts of crosslinker content.

The composition according to the invention preferably comprises one or more additional monomers. A suitable additional monomer is an ionic monomer, preferably a cationic monomer. Additional monomers, when present, are preferably included in an amount of up to 10% by weight.

A preferred cationic monomer is a quaternary ammonium salt. An especially preferred cationic monomer is (3-acrylamidopropyl)trimethyl ammonium chloride or [2-(acryloyloxy)ethyl]trimethyl ammonium chloride.

Plasticiser

The compositions according to the invention generally comprise, in addition to a crosslinked polymeric network, an aqueous plasticising medium. Plasticisers are generally used in the invention to control adhesive properties.

The aqueous plasticising medium optionally additionally comprises a polymeric or non-polymeric polyhydric alcohol (such as glycerol), an ester derived therefrom and/or a polymeric alcohol (such as polyethylene oxide). Glycerol is the preferred plasticiser. An alternative preferred plasticiser is an ester derived from boric acid and a polyhydric alcohol (such as glycerol). The aqueous reactive mixture preferably comprises from 10% to 50%, preferably from 10% to 45%, of plasticiser (other than water) by weight of the mixture.

One advantage of this invention is that it provides hydrogel dressings that are adhesive to dry skin which have water activities from 0.4 to 0.85, preferably from 0.65 to 0.8 and more preferably from 0.7 to 0.8. The latter materials have a greater tendency to wet (i.e. donate water to the skin) rather than to extract. These materials do not encourage the growth of microbial agents and they can be sterilised. Hydrogels based on the curing of ionic monomers are preferred as they enable a greater control of the activity of water. For materials with requirements for higher water activities, e.g. from 0.75 to 0.85, monomers which are potassium salts are preferred, e.g. SPA, K AMPS, and K acrylate.

The water activity of the bioadhesive composition is ideally selected to suit the wound to which the dressing is to be applied. Thus different compositions may be provided for application to different kinds of wounds such as burns and cuts. The water activity, and thus absorption characteristics, of the composition are optimised to prevent drying of the wound or to absorb excess exudate from the wound.

Interpenetrants

The compositions preferably additionally comprise a water soluble polymer suitable for forming an interpenetrating polymer network. Hydrogels based on interpenetrating polymer networks (IPN) are well known. An IPN has been defined as a combination of two polymers, each in network form, at least one of which has been synthesised and/or crosslinked in the presence of the other. As will be appreciated, this combination will generally be a physical combination rather than a chemical combination of the two polymers. IPN systems may be described by way of example as follows:

Monomer 1 is polymerised and crosslinked to give a polymer which is then swollen with monomer 2 plus its own crosslinker and initiator.

If only one polymer in the system is crosslinked the network formed is called a semi-IPN. Although they are also known as IPN's, it is only if there is total mutual solubility that full interpenetration occurs. In most IPN's there is, therefore, some phase separation but this may be reduced by chain entanglement between the polymers. It has also been reported that semi IPN's can be made in the presence of carrier solvents (for example water in the case of hydrophilic components).

It has been found that polymerising and crosslinking water soluble monomers in the presence of water soluble polymers, water and polyhydric alcohols produces hydrogel materials with enhanced rheological and consequently adhesive properties.

Suitable water soluble polymers for the formation of semi IPN's include poly (2-acrylamido-2-methylpropanesulphonic acid) or one of its salts and its copolymers, poly (acrylic acid-(3-sulphopropyl) ester potassium salt), copolymers of NaAMPS and SPA, polyacrylic acid, polymethacrylic acid, polyethylene oxide, polyvinyl methyl ether, polyvinyl alcohol, polyvinylpyrrolidone, its copolymers with vinyl acetate, dimethylaminoethyl methacrylate, terpolymers with dimethylaminoethyl methacrylate and vinylcaprolactam, polysaccharides such as gum arabic, karaya gum, xanthan gum, guar gum, carboxymethyl cellulose (CMC), NaCMC, hydroxypropylmethyl cellulose (HPMC), hydroxyethyl cellulose (HEC) or combinations thereof.

The amount of interpenetrant polymer used will be dependent on the mechanical and rheological properties required as well on consideration of processing conditions. If the interpenetrant polymer used increases the viscosity of the pre-gel mix beyond 5000 centipoise it has been found that the monomers do not polymerise and crosslink on an acceptable time scale (should be less than 60 seconds, preferably less than 10 seconds). The viscosity depends on the nature and molecular weight of the interpenetrant and the nature of pre-gel processing.

Of the natural polysaccharides, gum arabic or maltodextrin is usually preferred due to its cold water solubility and lesser effect on viscosity compared with, for example, karaya gum. A higher concentration of gum arabic than karaya may therefore be used if desired, enabling a wider control of hydrogel properties. It has also been found that the processing steps for assembling the pre-gel formulation can be critical with respect to the properties of the manufactured hydrogel. For a given formulation, if the components are assembled at 25° C. and cured different adhesive properties are obtained compared to those that have been heated to 70° C. Solutions containing natural polysaccharides become less opaque indicative of improved solubility. The activity of water in compositions prepared from heat treated pre-gels generally is lower than in non heat treated pre-gels.

Other Additives

The composition preferably comprises a hydrophobic polymer. Hydrophobic polymers may be incorporated either in the presence or absence of interpenetrant polymers to form phase separated materials. The preparation of two phase composites consisting of a hydrophilic polymer containing an ionically conducting continuous phase and domains of a hydrophobic pressure sensitive adhesive which enhance adhesion to mammalian skin have been reported in U.S. Pat. No. 5,338,490. The method of preparation described therein involved casting a mixture (as a solution and or suspension) consisting of the hydrophilic polymer containing phase and hydrophobic components onto a substrate and then removing the solvent. It has been found, however, that adhesive ionically conducting hydrogels may be better prepared by combining the hydrophobic polymer (preferably as an emulsion) with the components of the pre-gel reaction mixture and casting these onto a substrate and curing. In other words, there is no need to remove a solvent in order to form useful materials. Furthermore, the hydrophilic phase of the composition in addition to being a crosslinked network may also be an IPN or semi IPN.

It is believed that when hydrophobic polymers are incorporated in this way that the hydrophobic component segregates to the surface (as determined by Fourier transform infrared attenuated total reflectance spectroscopy, FTIR ATR, approximate sampling depth 1 $\mu$m using a ZnSe crystal or 0.25 $\mu$m with a Germanium crystal) and that it is the amount of the hydrophobic component present in the surface that influences the adhesion to a wide variety of materials. The greater the amount of the hydrophobic component in the surface the greater the adhesion. In U.S. Pat. No. 5,338,490 weight ratios of the hydrophilic phase to the hydrophobic phase of 60:1 to 8:1 were claimed. In hydrogel adhesives of between 100 to 2000 microns thick made in accordance with the present invention, ratios of hydrophilic to hydrophobic components ranging from 7:1 to 1:20 have been found to be preferable, especially when these ratios are present in the surface of the adhesive composition. In the process of the present invention, however, it may take up to 72 hours from the initial curing of the adhesive hydrogel for the segregation of the hydrophobic materials to the surface, as defined by the ATR sampling depth, to be complete.

Preferably, the hydrophobic pressure sensitive adhesive in such embodiments is selected from the group consisting of polyacrylates, polyolefins, silicone adhesives, natural or synthetically derived rubber base and polyvinyl ethers or blends thereof. Preferably the hydrophobic pressure sensitive adhesive in these embodiments is an ethylene/vinyl acetate copolymer such as that designated DM137 available from Harlow Chemicals or vinyl acetate dioctyl maleate such as that designated Flexbond 150 and sold by Air Products. Those skilled in the art will also know that the molecular weight and comonomer ratios may be altered to control the properties of hydrophobic pressure sensitive adhesives. In general, the degree of surface segregation exhibited by such hydrophobic pressure sensitive adhesive (HPSA) will be dependent on factors such as composition of the HPSA, viscosity of the pre-gel mixture, temperature and rate of curing.

The bioadhesive composition according to the invention preferably is such that the relative amount of hydrophobic polymer (which is the amount of hydrophobic polymer relative to the amount of monomer) is preferably at least four times greater, more preferably at least eight times greater, at the surface of the composition compared to what it is in the bulk of the composition. The relative amount at the surface is preferably the relative amount in the composition at a depth of up to 1 micron (as measured using FTIR ATR using a ZnSe crystal), preferably up to 0.25 micron (as measured using FTIR ATR using a Germanium crystal). The relative amount is measured by obtaining the ratio of the peak height of the peak in the carbonyl region for the hydrophobic polymer to the peak height of the peak in the carbonyl region for the first monomer, using the relevant FTIR ATR technique. The wave number values for the relevant peaks for the hydrophobic polymer and the monomer are well known.

More preferably, the ratio of the relative amount in the surface of the composition at a depth of up 0.25 micron to the relative amount in the surface of the composition at a depth of up 1 micron is more than 1:1, more preferably more than 1.25:1, most preferably more than 1.5:1.

Surfactant

The composition according to the invention optionally includes a surfactant.

Any compatible surfactant may be used. Nonionic, anionic and cationic surfactants are preferred, either alone or in combination. The surfactant is preferably included in an amount from 0.1% to 20% by weight, more preferably 0.1% to 10% by weight.

Carrier Material

The carrier material used in the wound dressings according to the invention is preferably perforated. Generally any conventional carrier material known for use in dressings can be used as the carrier material. It is preferable that the carrier material is made from inelastic fibres, preferably continuous inelastic fibres. The carrier material is generally either knitted, extruded, woven or non-woven. It is optionally in the form of, for example, a foam or a film. The smallest dimension of each perforation in the carrier material is preferably from 0.5 to 5.0 mm, more preferably from 1.0 to 3.0 mm. The fibres are made from cotton, rayon, polyester, polyamide, polypropylene, polyamide or wool or a mixture thereof.

Preparation of Wound Dressing

There are a variety of possible ways in which the process of the invention may be carried out.

Examples of ways in which process (a) may be performed include extruding the aqueous reaction mixture onto a web which, in the case of an automated process, is preferably moving. The web is preferably made from paper, polyester, polyolefin or any other material commonly used in the art. The carrier material is either laid on top of the aqueous reaction mixture after it has been extruded or is laid on top of the web and the aqueous reaction mixture is extruded over it. The assembly is then cured. Where the carrier material is perforated, it may be necessary to blow air through the assembly before curing to ensure that the perforations are free from the bioadhesive composition.

An alternative way in which process (a) according to the invention may be carried out is by coating the carrier material with the aqueous reaction mixture by, for example, dipping the carrier material in a bath of the aqueous reaction mixture and then passing the coated carrier material over or round a single roller or through a nip roller. The assembly is then cured. Again, if the carrier material is perforated, it may be necessary to blow air through the assembly before curing to ensure that the perforations are free from the bioadhesive composition.

Process (b) according to the invention may be performed, for example, by laminating a sheet of the bioadhesive composition with the carrier material. The sheet of bioadhesive composition is preferably supported by a plastic or coated material to act as a protective release sheet.

In both processes according to the invention, the aqueous reaction mixture is preferably coated in an amount of from 0.1 to 2 kg/m$^2$.

The wound dressing according to the invention is optionally coated on one or both sides with at least one release sheet. The release sheets are generally either made of plastic or coated paper e.g. siliconised paper.

The invention will be further described with reference to FIGS. 1 to 5 of the accompanying drawings and the following Examples in connection with bioadhesive compositions suitable for use in wound dressings.

EXAMPLE 1

In 20 parts of polyethylene glycol diacrylate (pEG600) (product of UCB Chemicals marketed under the trade name designation of Ebacryl 11) were dissolved 6 parts of 1-hydroxycyclohexyl phenyl ketone (product of Ciba and marketed under the trade name designation of Iracure 184). The solution so produced is herein designated solution A (XL/PI). Separately, 50 parts of the potassium salt of 3-sulphopropyl acrylate (SPA) (product of Raschig) were dissolved in 50 parts water to form solution B. A further solution designated solution C consisted of 50 parts water, 50 parts of the sodium salt of 2-acrylamido-2-methylpropane sulphonic acid (NaAMPS) product of the Lubrizol Corporation and marketed as a 50% aqueous solution under the trade name LZ2405). Mixtures of solutions B and C in the ratios of 100:0, 90:10, 60:40, 50:50, 40:60, 10:90 and 0:100 were made to form pre-gel solutions. To 80 parts of each of these pre-gel solutions, 0.15 parts of solution A, 5 parts potassium chloride and 20 parts distilled water were added. The pre-gel solutions were coated onto siliconised release paper at a coat weight of 0.8 kilograms per square meter and exposed to ultraviolet radiation by being passed under a medium pressure mercury arc lamp at a speed of 5 meters per minute to form clear self supporting gels. The residence time under the lamp was 4 seconds. The storage moduli(G') of 20 mm diameter discs stamped from the gels were recorded on a Rheometric Scientific RS-5 rheometer at 37° C. The G' values at 1rad are recorded in Table 1. With the exception of the gels containing 90 and 100 parts SPA, the gels produced had acceptable tack and peel properties on the skin. From the data in Table 1 relatively linear changes in storage modulus are obtained on increasing or decreasing the SPA to NaAMPS ratio.

The gels were found to lose adhesion on water uptake and are thus suitable for use in wound dressings.

In the above Example, and in the following Examples wherever parts are mentioned they are meant as parts by weight unless otherwise specified.

TABLE 1

| NaAMPS Solution C | 80 | 72 | 48 | 40 | 32 | 8 | 0 |
|---|---|---|---|---|---|---|---|
| SPA Solution B | 0 | 8 | 32 | 40 | 48 | 72 | 80 |
| Distilled Water | 20 | 20 | 20 | 20 | 20 | 20 | 20 |
| XL/PI Solution A | 0.15 | 0.15 | 0.15 | 0.15 | 0.15 | 0.15 | 0.15 |
| KCl | 5 | 5 | 5 | 5 | 5 | 5 | 5 |
| G'(Pa) @ 1 rad/s | 4,198 | 3,389 | 2,471 | 2,205 | 1,759 | 703 | 492 |

EXAMPLE 2

In 20 parts of polyethylene glycol diacrylate (pEG600) (product of UCB Chemicals marketed under the trade name designation of Ebacryl 11) 6 parts of 1-hydroxycyclohexyl phenyl ketone (product of Ciba and marketed under the trade name designation of Irgacure 184) were dissolved. (This solution is designated solution A) (XL/PI). Separately 58 parts of the potassium salt of 3-sulphoproylacrylate (SPA) (product of Raschig) were dissolved in 58 parts distilled water to form solution D. A further solution designated solution E consisted of 42 parts water, 58 parts of the sodium salt of 2-acrylamido-2-methylpropane sulphonic acid (NaAMPS) (a product of the Lubrizol Corporation marketed as a 58% aqueous solution under the trade name LZ2405A). Mixtures of solutions D and B in the ratios 100:0, 90:10, 60:40, 50:50, 40:60, 10:90 and 0:100 were made to form pre-gel solutions. To 100 parts of each of these pre-gel solutions, 0.17 parts of solution A and 3 parts potassium chloride were added. The pre-gel solutions were coated onto siliconised release paper at a coat weight of 0.8 kilograms per square meter and passed under a medium pressure mercury arc lamp at a speed of 5 meters per minute to form clear self-supporting gels. Storage moduli were measured as in Example 1 and are recorded in Table 2. As in the gels described in Example 1 the changes in the elastic or storage modulus G'(Pa) are linear with respect to the increasing or decreasing ratio of NaAMPS to SPA. All the gels produced possess acceptable tack and peel strength against skin. The gels with NaAMPS:SPA ratios in the range of 60:40 to 40:60, however, have a better balance of reusability and peel strength.

The gels were found to lose adhesion on water uptake and are thus suitable for use in wound dressings.

TABLE 2

| NaAMPS Solution E | 100 | 90 | 60 | 50 | 40 | 10 | 0 |
|---|---|---|---|---|---|---|---|
| SPA Solution D | 0 | 10 | 40 | 50 | 60 | 90 | 100 |
| XL/PI Solution A | 0.17 | 0.17 | 0.17 | 0.17 | 0.17 | 0.17 | 0.17 |
| KCl | 3 | 3 | 3 | 3 | 3 | 3 | 3 |
| G'(Pa) @ 1 rad/s | 15,142 | 14,333 | 11,073 | 10,672 | 9,920 | 6,280 | 5,199 |

Upon varying the amount of the cross-linking agent a substantially linear change in the elastic modulus G' can also be obtained, as illustrated by the graph of FIG. 1.

EXAMPLE 3

To 57 parts of a 58% solution of the sodium salt of 2-acrylamido-2-methylpropane sulphonic acid (NaAMPS) (LZ2405A) 10 parts of a 58% solution of the potassium salt of 3-sulphopropyl acrylate (SPA) were added along with 5 parts potassium chloride and stirred until the potassium chloride has dissolved. This solution was then mixed with 30 parts glycerol for 30 minutes. To the latter solution were added 0.15 parts of a solution containing 20 parts of polyethylene glycol diacrylate (pEG600) (product of UCB Chemicals marketed under the trade name designation of Ebacryl 11) in which 6 parts of 1-hydroxycyclohexyl phenyl ketone (product of Ciba and marketed under the trade name designation of Irgacure 184) were dissolved. The so-formed pre-gel solution was then cured as in Example 1. The gels were found to lose adhesion on water uptake and are thus suitable for use in wound dressings. Good skin adhesion properties were obtained for this gel.

EXAMPLE 4

The method of Example 3 was repeated with 1 part citric acid being added with the potassium chloride. The adhesion to skin and reusability characteristics for this gel of Example 4 containing citric acid and SPA were better than the gel described in Example 3.

EXAMPLE 5

The formulations listed in Table 4 were prepared using the following method which is for formulation 5a. To 58 parts of a 50% aqueous solution of the sodium salt of 2-acrylamido-2-methylpropane sulphonic acid (NaAMPS) (LZ2405) 2 parts of the potassium salt of 3-sulphopropyl acrylate (SPA) were added along with 1.575 parts of acrylic acid and stirred. This solution was then mixed with 37 parts glycerol for 30 minutes. To the latter solution were added 0.175 parts of solution (F). Solution F contains 20 parts of an alkoxylated triacrylate (product of UCB Chemicals marketed under the trade name designation of IRR 210) in which 1.4 parts of 1-hydroxycyclohexyl phenyl ketone (product of Ciba and marketed under the trade name designation of Irgacure 184) are dissolved. The so-formed pre-gel solution was then cured as in Example 1. The G' and G" moduli were measured from 20 mm diameter discs of the gel using a Rheometric Scientific RS-5 rheometer at 37° C.

To prepare formulation 5b, the same method was repeated except that 0.15 parts of solution F were used instead of 0.175 parts.

To prepare formulations 5c and 5d, the same method used for formulation 5a was repeated except that the parts by weight were changed to the figures given in Table 4A. The potassium chloride was added instead of the acrylic acid; for formulation 5d, deionised water was also added.

TABLE 4

| | Composition in parts by weight | | | |
|---|---|---|---|---|
| Formulation | 5a | 5b | 5c | 5d |
| 50% NaAMPS | 58 | 58 | 75 | 75 |
| KCl | | | 5 | 5 |
| Acrylic Acid | 1.575 | 1.575 | | |
| SPA | 2 | 2 | 2 | 2 |
| Glycerol | 37 | 37 | 25 | 25 |
| DI WATER | | | | 3 |
| PI/XL (Solution) | 0.175 (F) | 0.15 (F) | 0.15 (A) | 0.15 (A) |
| G' (Pa) @ 1 rad/s | 1455 | | 1054 | |
| G' (Pa) @ 100 rad/s | 5174 | | 4613 | |
| G" (Pa) @ 1 rad/s | 601 | | 488 | |
| G" (Pa) @ 100 rad/s | 2906 | | 2640 | |

EXAMPLE 6

The formulations listed in Table 5 were prepared using the following method which is for formulation 6a. To 67 parts of a 58% aqueous solution of the sodium salt of 2-acrylamido-2-methylpropane sulphonic acid (NaAMPS) (LZ2405A) 2 parts of the potassium salt of 3-sulphopropyl acrylate (SPA) were added along with 5 parts of potassium chloride and 1 part of citric acid and stirred until the potassium chloride had dissolved. This solution was then mixed with 30 parts glycerol for 30 minutes. To the latter solution were added 0.13 parts of solution A prepared as described in Example 1. The so-formed pre-gel solution was then cured as in Example 1. The G' and G" moduli were measured from 20 mm diameter discs of the gel using a Rheometric Scientific RS-5 rheometer at 37° C.

To prepare formulation 6b, the same method was repeated except that the potassium chloride and citric acid were omitted, 0.06 parts by weight of solution G were used instead of solution A and the amounts of the other ingredients were changed to the amounts given in Table 5. Solution G contains 20 parts of polyethylene glycol diacrylate (molecular weight 400) (product of UCB Chemicals marketed under the trade name designation of IRR 280) in which 6 parts of 1-hydroxycyclohexyl phenyl ketone (product of Ciba and marketed under the trade name designation of Irgacure 184) are dissolved.

To prepare formulations 6c and 6d, the same method used for formulation 6a was repeated except that citric acid was omitted, 0.06 parts of solution G were used instead of solution A and the parts by weight were changed to the figures given in Table 5.

To prepare formulation 6e, the same method used for formulation 6a was repeated except that gum arabic and the ethylene/vinyl acetate copolymer designated DM137 and sold by Harlow Chemicals were added instead of citric acid and the parts by weight were changed to the figures given in Table 5.

To prepare formulation 6f, the same method used for formulation 6a was repeated except that the ethylene/vinyl acetate copolymer designated DM137 and sold by Harlow Chemicals, polyethylene glycol (molecular weight 400) and sodium nitrate were added with the citric acid and the parts by weight were changed to the figures given in Table 5.

TABLE 5

| Formulation | Composition in parts by weight | | | | | |
|---|---|---|---|---|---|---|
| | 6a | 6b | 6c | 6d | 6e | 6f |
| 58% NaAMPS | 67 | 57 | 57 | 57 | 67 | 50 |
| KCl | 5 | | 5 | 5 | 5 | 1 |
| Citric Acid | 1 | | | | | 1 |
| SPA | 2 | 10 | 10 | 10 | 2 | 18 |
| Glycerol | 30 | 33 | 33 | 28 | 30 | 20 |
| Gum Arabic | | | | | 2 | |
| DM 137 | | | | | 2 | 3 |
| PEG 400 | | | | | | 10 |
| Sodium Nitrate | | | | | | 0.05 |
| PI/XL (Solution) | 0.13 (A) | 0.06 (G) | 0.06 (G) | 0.075 (G) | 0.25 (A) | 0.175 (A) |
| G'(Pa) @ 1 rad/s | 2973 | 4326 | | 3019 | 4637 | |
| G'(Pa) @ 100 rad/s | 9800 | 13986 | | 9763 | 8789 | |
| G"(Pa) @ 1 rad/s | 1265 | 1914 | | 1200 | 1029 | |
| G"(Pa) @ 100 rad/s | 4597 | 6707 | | 4537 | 3952 | |

EXAMPLE 7

To 34.7 parts of a 58% aqueous solution of the sodium salt of 2-acrylamido-2-methylpropane sulphonic acid (NaAMPS) (LZ2405A) 34.7 parts of a 58% aqueous solution of the potassium salt of 3-sulphoproyl acrylate (SPA) were added along with 4.6 parts potassium chloride and 3 parts distilled water and stirred until the potassium chloride has dissolved. This solution was then mixed with 23.2 parts glycerol for 30 minutes. To the latter solution were added 0.15 parts of solution A prepared as described in Example 1. The so-formed pre-gel solution was then cured as in Example 1. The gels were found to lose adhesion on water uptake and are thus suitable for use in wound dressings.

EXAMPLE 8

To 20 parts glycerol, 3 parts of a hydrophobic ethylene/vinyl acetate copolymer emulsion (50% solids) (product of Harlow Chemicals marketed under the trade name DM137) and 10 parts polyethylene glycol (molecular weight 600) were added and stirred until a uniform colour was obtained. To this mixture were added 50 parts of a 58% solution of the sodium salt of 2-acrylamido-2-methylpropane sulphonic acid (NaAMPS) (LZ2405A), 16 parts potassium salt of 3-sulphopropyl acrylate (SPA) and 5 parts potassium chloride, and the solution was heated with stirring to 60° C. for one hour. The mixture had changed from an opaque off white to a translucent off white appearance. The turbidity of the solutions as measured in a portable turbidity meter, product code H193703 marketed by Hanna had changed from 254 ftu to 107 ftu. The solution was cooled to 20° C. and then there was added 0.13 parts of solution A prepared as described in Example 1. This final solution was stirred for one hour and then cured as in Example 1. The resulting gel had a G' value at 1 rad of 5328 Pa. The activity of water in the gel, as determined by placing the gel into cabinets at varying levels of humidity at 40° C. (40, 52, 64 and 80% RH) and measuring weight uptake or loss and extrapolating to zero weight chance, was 0.62. The adhesion to skin of this gel was significantly greater than those described in the previous examples. The gels were found to lose adhesion on water uptake and are thus suitable for use in wound dressings. Analysis of the gel by attenuated total reflectance infra-red spectroscopy revealed that in the surface regions (about 1 micron or less), either the air surface or the surface in contact with the release paper, the concentration of the ethylene/vinyl acetate copolymer relative to the NaAMPS was significantly enhanced compared to the bulk composition.

EXAMPLE 9

The method of Example 8 was carried out except that with the glycerol were added 3 parts of gum arabic. The resulting gel had a G' value at 1 rad of 5406 Pa. The activity of water as determined by the method in Example 8 was 0.55. The adhesion to skin of this gel was significantly greater than those described in the previous examples. The gels were found to lose adhesion on water uptake and are thus suitable for use in wound dressings. Analysis of the gel by attenuated total reflectance infra-red spectroscopy revealed that in the surface region (about 1 micron or less), either the air surface or the surface in contact with the release paper, the concentration of the ethylene/vinyl acetate copolymer relative to the NaAMPS was significantly enhanced compared to the bulk composition.

EXAMPLE 10

The formulations shown in Tables 6 and 7 were prepared using the following method which is for formulation 10a. To 20 parts glycerol, 15 parts of a hydrophobic vinyl acetate/dioctyl maleate copolymer emulsion (product of Air Products marketed under the trade name Flexbond 150) were added and stirred until a uniform colour was obtained. To this mixture were added 44 parts of a 58% solution of the sodium salt of 2-acrylamido-2-methylpropane sulphonic acid (NaAMPS) (LZ2405A), 20 parts potassium salt of 3-sulphopropyl acrylate (SPA) and 4 parts potassium chloride, and the solution was heated with stirring to 60° C. for one hour. The solution was cooled to 20° C. and then there was added 0.13 parts of solution G prepared as described in Example 6. This final solution was stirred for one hour and then cured as in Example 1. The G' and G" moduli were measured from 20 mm diameter discs of the gel using a Rheometric Scientific RS-5 rheometer at 37° C.

Figure 2:
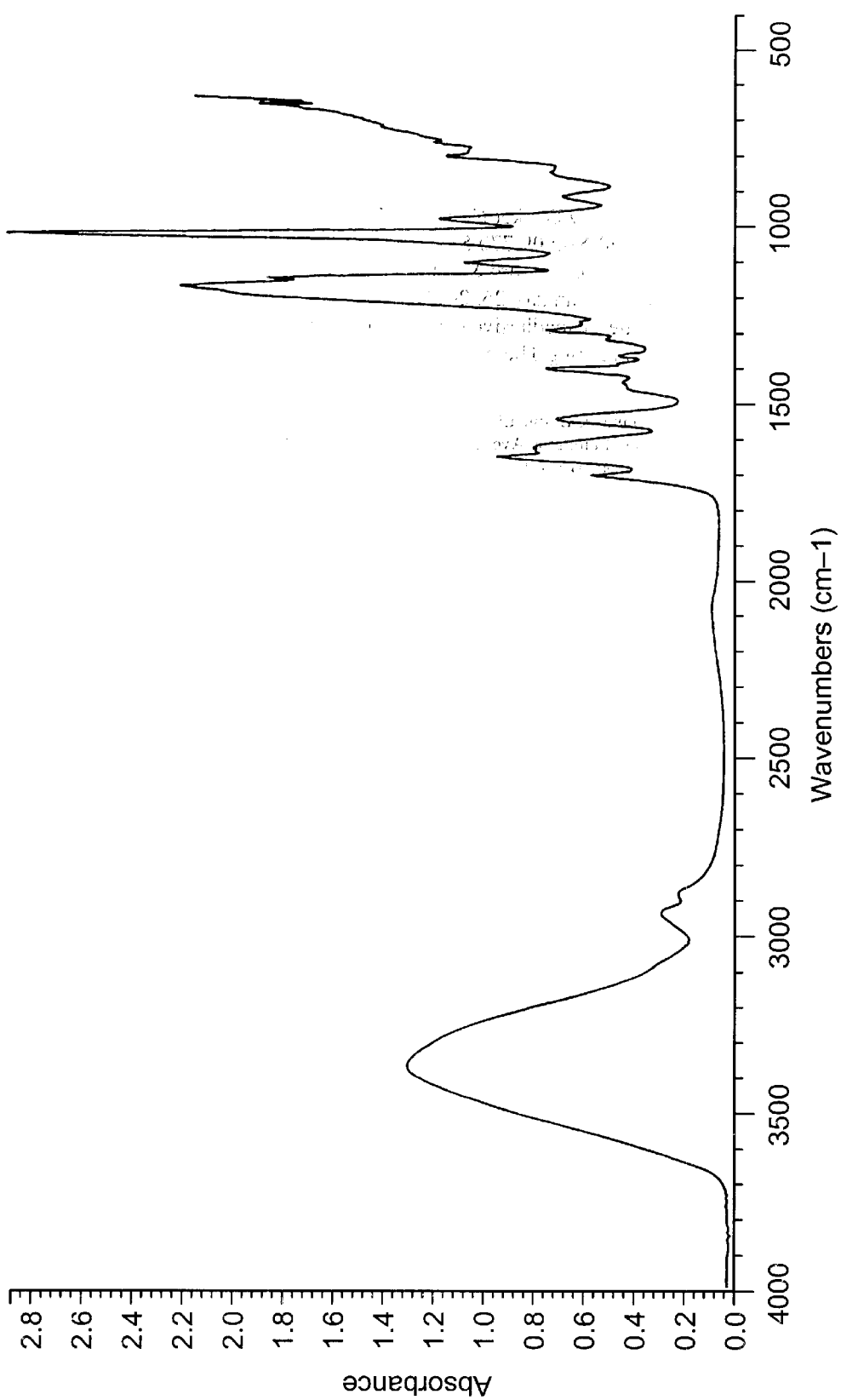
FIG. 2 depicts the fourier transform infrared attentuated total reference (FTIR ATR) spectra of the pregel mixture described in example 10a. The FTIR ATR spectra was obtained using a ZnSe crystal and an approximate sampling depth of 1 $\mu$m.
Figure 3:
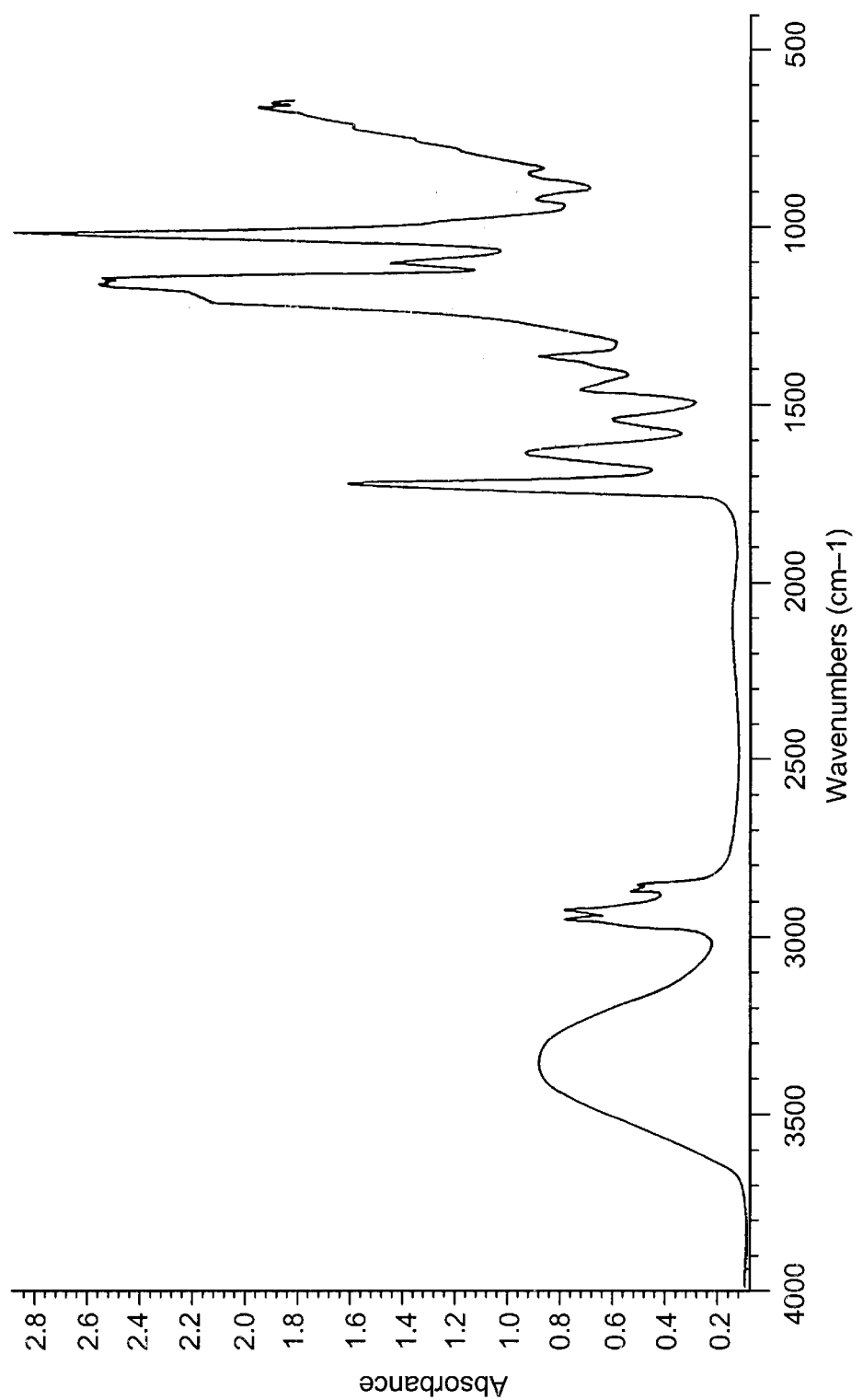
FIG. 3 depicts the fourier transform infrared attentuated total refernce (FTIR ATR) spectra for the gel of Example 10a that is formed after polymerization. The FTIR ATR spectra was obtained using a ZnSe crystal and an approximate sampling depth of 1 $\mu$m.

Fourier transform infrared attenuated total reflectance spectra (FTIR ATR) were taken of both the pregel mixture and of the gel formed after polymerisation using a ZnSe crystal (approximate sampling depth 1 μm). The results obtained are shown in FIGS. 2 and 3, respectively. The peak at around 1740 cm$^{-1}$ corresponds to the hydrophobic polymer whereas the peak at around 1550 cm$^{-1}$ corresponds to NaAMPS. It can be seen that before polymerisation the ratio in height of the former peak to the latter peak is about 0.25:1 whereas after polymerisation, the ratio is about 2.9:1. This shows a twelve-fold increase in the concentration of the hydrophobic polymer at the surface of the gel after polymerisation indicating that the hydrophobic polymer surface segregates. A further FTIR ATR spectrum was taken of the gel formed after polymerisation using a germanium crystal (approximate sampling depth 0.25 μm). It was found that the ratio in the height of the former peak to the latter peak is 3.9:1 showing a sixteen fold increase in the concentration or the hydrophobic polymer on the surface of the gel.

To prepare formulation 10b, the same method used for formulation 10a was repeated except that a hydrophobic ethylene/vinyl acetate copolymer emulsion (50% solids) (product of Harlow Chemicals marketed under the trade name DM137) was used instead of Flexbond 150, 3 parts polyethylene glycol (molecular weight 600) were added with the hydrophobic copolymer DM137 and the parts by weight were changed to the figures given in Table 6.

Figure 4:
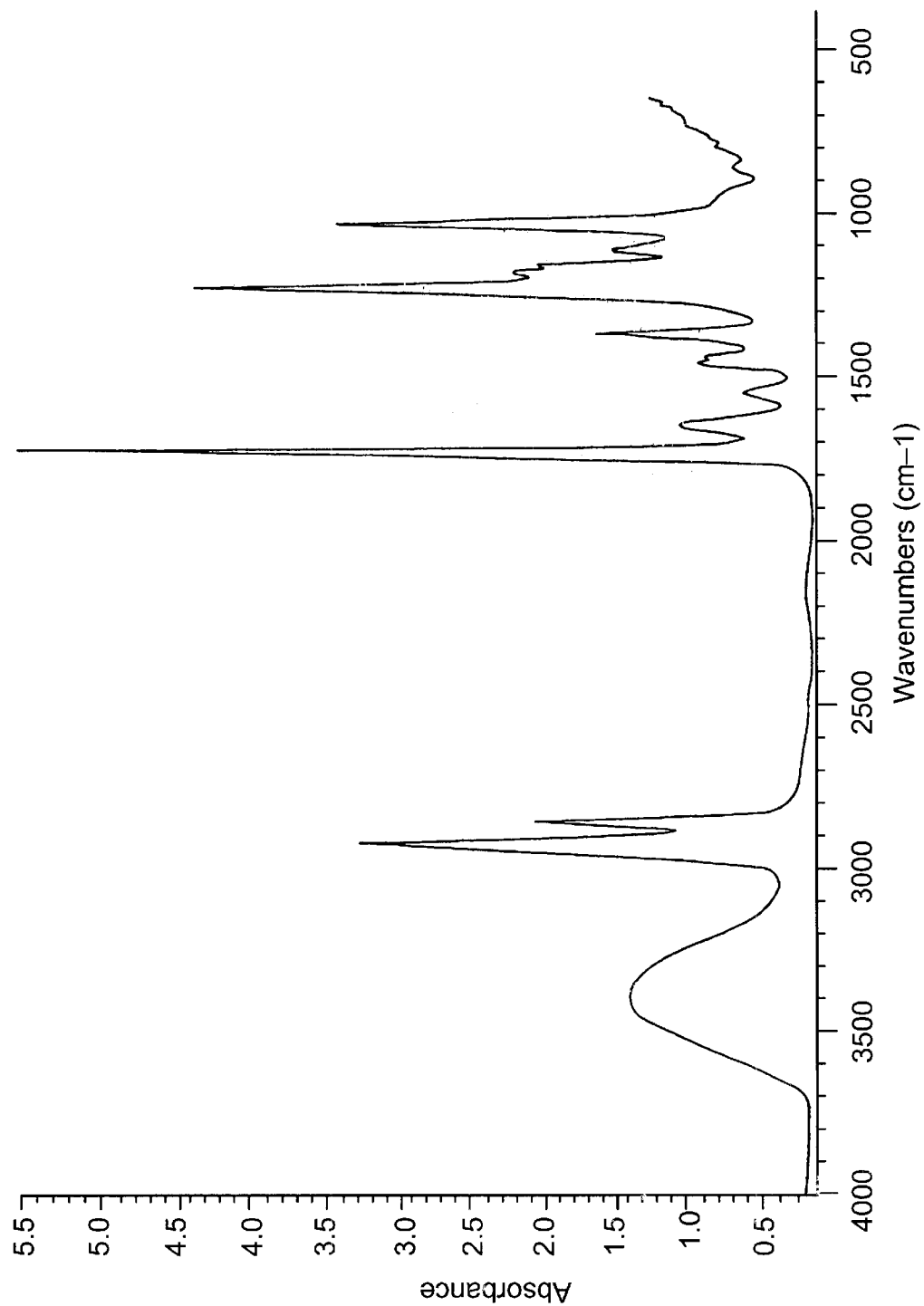
FIG. 4 depicts the fourier transform infrared attentuated total reference (FTIR ATR) spectra for the gel of Example 10b that is formed after polymerization. The FTIR ATR spectra was obtained using a ZnSe crystal and an approximate sampling depth of 1 $\mu$m.

FTIR ATR were taken of the gel formed after polymerisation using a ZnSe crystal (approximate sampling depth 1 μm) and a germanium crystal (approximate sampling depth 0.25 μm). The results obtained are shown in FIGS. 4 and 5, respectively. As for formulation 10a, the peak at around 1740 cm$^{-1}$ corresponds to the hydrophobic polymer whereas the peak at around 1550 cm$^{-1}$ corresponds to NaAMPS. The ratio of the former peak to the latter peak for FIG. 4 (the ZnSe FTIR ATR spectrum) is about 21:1 whereas the ratio for FIG. 5 (the germanium FTIR ATR spectrum) is about 11:1. This again demonstrates the hydrophobic polymer segregates to the surface of the gel.

To prepare formulation 10c, the same method used for formulation 10a was repeated except that a hydrophobic ethylene/vinyl acetate copolymer emulsion (50% solids) (product of Harlow Chemicals marketed under the trade name DM137) was used instead of Flexbond 150, 0.05 parts of sodium nitrate were added with the potassium chloride and the parts by weight were changed to the figures given in Table 6.

To prepare formulations 10d and 10e, the same method used for formulation 10b was repeated except that solution A as described in Example 1 was used instead of solution G and the parts by weight were changed to the figures given in Table 6.

To prepare formulations 10f and 10g, the same method used for formulation 10d was repeated except that potassium chloride was omitted and the parts by weight were changed to the figures given in Table 6.

TABLE 6

| COMPOSITION by WEIGHT | | | | | | | |
|---|---|---|---|---|---|---|---|
| Formulation | 10a | 10b | 10c | 10d | 10e | 10f | 10g |
| 58% NaAMPS | 44 | 44 | 65 | 35 | 35 | 35 | 37 |
| KCl | 4 | 5 | 5 | 5 | 5 | | |
| SPA | 20 | 20 | 10 | 25 | 25 | 15 | 18 |
| Glycerol | 20 | 20 | 23 | 20 | 20 | 30 | 30 |
| Gum Arabic | | | | | | | |
| DM 137 | | 15 | 2 | 15 | 15 | 15 | 10 |
| Flexbond 150 | 15 | | | | | | |
| PEG 600 | | 3 | | 10 | 10 | 5 | 5 |
| Sodium Nitrate | | | 0.05 | | | | |
| PI/XL | 0.13 | 0.13 | 0.15 | 0.12 | 0.13 | 0.15 | 0.15 |

TABLE 6-continued

| COMPOSITION by WEIGHT | | | | | | | |
|---|---|---|---|---|---|---|---|
| Formulation | 10a | 10b | 10c | 10d | 10e | 10f | 10g |
| (Solution) | (G) | (G) | (G) | (A) | (A) | (A) | |
| G'(@ 1 rad/s) | 6156 | 4756 | | | | | |
| G'(@ 100 rad/s) | 15219 | 15412 | | | | | |
| G"(@ 1 rad/s) | 1775 | 1840 | | | | | |
| G"(@ 100 rad/s) | 5748 | 7743 | | | | | |

To prepare formulations 10h, 10i and 10j, the same method used for formulation 10g was repeated except that the parts by weight were changed to the figures given in Table 7.

To prepare formulations 10k, 10l and 10m, the same method used for formulation 10j was repeated except that a propylene oxide/ethylene oxide block copolymer surfactant (designated PE/F127 and manufactured by BASF) was added with the glycerol and the parts by weight were changed to the figures given in Table 7.

TABLE 7

| COMPOSITION by WEIGHT | | | | | | |
|---|---|---|---|---|---|---|
| Formulation | 10h | 10i | 10j | 10k | 10l | 10m |
| 58% NaAMPS | 37 | 35 | 35 | 35 | 35 | 35 |
| SPA | 18 | 15 | 25 | 25 | 25 | 25 |
| Glycerol | 30 | 33 | 20 | 20 | 20 | 20 |
| DM 137 | 10 | 10 | 15 | 15 | 15 | 15 |
| PEG 600 | 10 | 5 | 10 | 10 | 10 | 10 |
| PE/F127 | | | | 1 | 5 | 9 |
| PI/XL (Solution) | 0.15(A) | 0.15(A) | 0.14(A) | 0.14(A) | 0.14(A) | 0.14(A) |

EXAMPLE 11

An aqueous reaction mixture (or so-called pregel) was prepared as described in Example 3 and coated onto a siliconised release paper at a coat weight of 0.8 kilograms per square meter. The aqueous reaction mixture was cured by passing the assembly under a medium pressure mercury arc lamp at a speed of 5 meters per minute. The residence time under the lamp was 4 seconds. The cured bioadhesive composition was then laminated by a polyurethane film (sold under the trade name SRF076 part number 93034 by Advanced Medical Solutions) to form a wound dressing.

As will be seen, the invention presents a number of different aspects and it should be understood that it embraces within its scope all novel and inventive features and aspects herein disclosed, either explicitly or implicitly and either singly or in combination with one another. Also, many detail modifications are possible and, in particular, the scope of the invention is not to be construed as being limited by the illustrative example(s) or by the terms and expressions used herein merely in a descriptive or explanatory sense.

What is claimed is:

1. A water unstable bioadhesive composition comprising:
   (i) a water activity in the range of 0.4 to 0.9;
   (ii) an elastic modulus at 1 rad/s in the range of 700 to 15,000 Pa;
   (iii) an elastic modulus at 100 rad/s in the range of 2000 to 40,000 Pa;
   (iv) a viscous modulus at 1 rad/s in the range of 400 to 14,000 Pa;

(v) a viscous modulus at 100 rad/s in the range of 1000 to 35,000 Pa;
wherein the viscous modulus is less than the elastic modulus in the frequency range of 1 to 100 rad/s.

2. A bioadhesive composition according to claim 1 which comprises an aqueous plasticiser, a copolymer of a hydrophilic unsaturated water-soluble first monomer, a hydrophilic unsaturated water-soluble second monomer together with a cross-linking agent, wherein said first monomer enhances the bioadhesive properties of said composition.

3. A bioadhesive composition according to claim 1 obtained by polymerising an aqueous reaction mixture comprising a hydrophilic unsaturated water-soluble first monomer, a hydrophilic unsaturated water-soluble second monomer, and a cross-linking agent, wherein said first monomer preferentially enhances the bioadhesive properties of the composition.

4. A bioadhesive composition according to claim 2 or claim 3 wherein said first monomer enhances the mechanical strength of said composition and/or said second monomer increases the water activity of said composition.

5. A bioadhesive composition according to claim 4 wherein said second monomer preferentially lowers the electrical impedance and enhances the electrical conductivity of said composition.

6. A bioadhesive composition according to claim 2 or 3 wherein said first monomer is a compound of formula

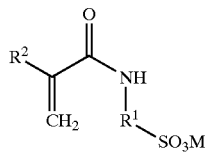

(I)

wherein $R^1$ is an optionally substituted hydrocarbon moiety, $R^2$ is hydrogen or an optionally substituted methyl and ethyl, and M is hydrogen or a cation.

7. A bioadhesive composition according to claim 6 wherein $R^1$ is an optionally substituted alkyl, cycloalkyl or aromatic moiety containing from 3 to 12 carbon atoms.

8. A bioadhesive composition according to claim 6 or claim 7 wherein R1 represents

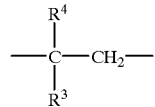

wherein $R^3$ represents hydrogen or an optionally substituted straight or branched chain alkyl group possessing from 1 to 6 carbon atoms and $R^4$ represents an optionally substituted straight or branched chain alkyl group possessing from 1 to 6 carbon atoms.

9. A would dressing which comprises a carrier material and a bioadhesive composition according to claim 1.

10. A wound dressing according to claim 11 which is coated by the bioadhesive compositions.

11. A method for preparing a wound dressing as defined in claim 10 comprising either:

(a) coating or encapsulating a carrier material with an aqueous reaction mixture comprising a hydrophilic unsaturated water-soluble first monomer, a hydrophilic unsaturated water-soluble second monomer together with a cross-linking agent, wherein said first monomer preferentially enhances the bioadhesive properites of the composition, and curing said coating on said carrier material; or (b) coating a carrier material with the bioadhesive composition of claim 1.

* * * * *

UNITED STATES PATENT AND TRADEMARK OFFICE
CERTIFICATE OF CORRECTION

PATENT NO. : 6,447,798 B1
DATED : January 26, 2001
INVENTOR(S) : Munro et al.

It is certified that error appears in the above-identified patent and that said Letters Patent is hereby corrected as shown below:

<u>Column 18,</u>
Line 20, Claim 9 should read as follows:
9. A bioadhesive composition according to claim 2 or 3 wherein the second monomer is a compound of formula:

(II)

wherein $R^5$ represents hydrogen or optionally substituted methyl or ethyl, $R^6$ represents hydrogen, a cation or $R^7SO_3$, wherein $R^7$ represents an optionally substituted alkylene moiety of 1 to 4 carbon atoms.

Signed and Sealed this

Fifth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,447,798 B1
DATED : January 26, 2001
INVENTOR(S) : Munro et al.

It is certified that error appears in the above-identified patent and that said Letters Patent is hereby corrected as shown below:

Column 18,
Line 20, Claim 9 should read as follows:
9. (Amended) A bioadhesive composition according to claim 2 or 3 any one of claims 2 to 8 wherein the second monomer is a compound of formula:

(II)

wherein $R^5$ represents hydrogen or optionally substituted methyl or ethyl, $R^6$ represents hydrogen, a cation or $R^7SO_3$, wherein $R^7$ represents an optionally substituted alkylene moiety of 1 to 4 carbon atoms.

Signed and Sealed this

Thirty-first Day of May, 2005

JON W. DUDAS
*Director of the United States Patent and Trademark Office*

Disclaimer

6,447,798 B1—Hugh Semple Munro, Chipping Camden; Mohammed Yasin, Saltley, both of (GB). BIOADHESIVE COMPOSITIONS AND WOUND DRESSINGS CONTAINING THEM. Patent dated Sept. 10, 2002. Disclaimer filed July 25, 2005, by the assignee, First Water Limited.

Hereby enters this disclaimer to claims 9, 10 and 11 of said patent.

*(Official Gazette, October 18, 2005)*

UNITED STATES PATENT AND TRADEMARK OFFICE
CERTIFICATE OF CORRECTION

PATENT NO.    : 6,447,798 B1
DATED         : January 26, 2001
INVENTOR(S)   : Hugh Semple Munro et al.

It is certified that error appears in the above-identified patent and that said Letters Patent is hereby corrected as shown below:

<u>Column 18,</u>
Lines 20 and 21, delete and insert the following:
-- 9.    A bioadhesive composition according to claim 2 or 3 any one of claims 2 to 8 wherein the second monomer is a compound of formula:

(II)

wherein $R^5$ represents hydrogen or optionally substituted methyl or ethyl, $R^6$ represents hydrogen, a cation or $R^7SO_3$, wherein $R^7$ represents an optionally substituted alkylene moiety of 1 to 4 carbon atoms. --.
Lines 22 and 23, delete and insert the following:
-- 10. A wound dressing which comprises a carrier material and a bioadhesive composition according to claim 1. --.
Lines 24-35, delete and insert the following:
-- 11. A wound dressing according to claim 1 which is coated by the bioadhesive compositions. --.

UNITED STATES PATENT AND TRADEMARK OFFICE
CERTIFICATE OF CORRECTION

PATENT NO. : 6,447,798 B1
DATED : January 26, 2001
INVENTOR(S) : Hugh Semple Munro et al.

It is certified that error appears in the above-identified patent and that said Letters Patent is hereby corrected as shown below:

<u>Column 18 (cont'd),</u>
Line 36, insert
-- 12. A method for preparing a wound dressing as defined in claim 11 comprising either:
    (a) coating or encapsulating a carrier material with an aqueous reaction mixture comprising a hydrophilic unsaturated water-soluble first monomer, a hydrophilic unsaturated water-soluble second monomer together with a cross-linking agent, wherein said first monomer perferentially enhances the bioadhesive properties of the composition, and curing said coating on said carrier material; or
    (b) coating a carrier material with the bioadhesive composition of claim 1. --.

This certificate supersedes Certificate of Correction issued May 31, 2005.

Signed and Sealed this

Sixth Day of December, 2005

JON W. DUDAS
*Director of the United States Patent and Trademark Office*

Disclaimer

6,447,798 B1—Hugh Semple Munro, Chipping Camden; Mohammed Yasin, Saltley, both of (GB). BIOADHESIVE COMPOSITIONS AND WOUND DRESSINGS CONTAINING THEM. Patent dated Sept. 10, 2002. Disclaimer filed July 25, 2005, by the assignee, First Water Limited.

Hereby enters this disclaimer to claims 9, 10 and 11 of said patent.

*(Official Gazette October 16, 2007)*